United States Patent [19]

Kürner

[11] 4,055,662

[45] Oct. 25, 1977

[54] ANTIMICROBIAL COMPOSITION CONTAINING 10-UNDECENSIC ACID ISOPROPYLIC ESTER

[76] Inventor: Rudolf Kürner, P.O. Box 1763, 638 Bad Homburg vor der Hohe, Germany

[21] Appl. No.: 619,507

[22] Filed: Oct. 3, 1975

[30] Foreign Application Priority Data

Oct. 5, 1974 Germany .............. 2447627

[51] Int. Cl.$^2$ ................................. A01N 9/24
[52] U.S. Cl. .................................. 424/312
[58] Field of Search ................ 424/312, 365

[56] References Cited

PUBLICATIONS

Materials Evaluated as Insecticides, Repellents, and Chemosterilants at Orlando and Gainesville, Fla., 1952–1964.
Agriculture Handbook No. 340, Aug. 1967, pp. 7, 342 and 343.
Panradl, Chem. Abst. vol. 51, (1957), p. 9087.

*Primary Examiner*—Allen J. Robinson
*Attorney, Agent, or Firm*—Cooper, Dunham, Clark, Griffin & Moran

[57] ABSTRACT

An antimicrobial composition comprising a therapeutically effective amount of 10-undecenoic acid isopropylic ester optionally together with usual pharmaceutically acceptable carriers and a method for the treatment of skin diseases by the topical administration of a therapeutically effective amount of 10-undecenoic acid isopropylic ester.

3 Claims, No Drawings

ANTIMICROBIAL COMPOSITION CONTAINING 10-UNDECENSIC ACID ISOPROPYLIC ESTER

The invention relates to a new antimicrobial composition, especially to a wide-spectrum antimicrobicum to be topically applied.

Subject of the invention is an antimicrobial composition characterized in that it comprises a therapeutically effective amount of 10-undecenoic acid isopropylic ester, and may optionally contain the usual pharmaceutically acceptable carriers. Such therapeutically effective compositions normally contain from 0.1 to 50 percent by weight, preferably 1 to 10 percent by weight of 10-undecenoic acid isopropylic ester, based on the total weight of the composition.

The formula of undecenoic acid isproplyic ester is

For therapeutic use 10-undecenoic acid isopropylic ester is employed per se or in formulations which contain usual pharmaceutically acceptable carriers or diluents.

Such compositions contain at least about 0.1 percent by weight undecenoic acid isopropylic ester, preferably about 0.5 to 50 percent by weight and especially preferred about 1 to 10 percent by weight, based on the total weight of the composition. For medicinal prophylaxis and for the post-treatment of acute diseased skin conditions, compositions containing an amount of less than about 0.1 percent by weight might be used. Pure undecenoic acid isopropylic ester may be employed with especially acute diseased skin conditions.

The isopropylic ester of the undecenoic acid has, compared to the other homologous esters of the aliphatic alcohols as well as to the phenolic ester, clear advantages with respect to application and therapeutics.

For use according to invention the 10-undecenoic acid isopropylic ester can be admixed with all usual pharmaceutically acceptable carriers. Thus it can, for instance, be used in the form of ointments, creams, powders, mixtures, shaking mixtures, lotions, oils and oily formulations, respectively as well as in the form of aerosols. Furthermore it can be used in cosmetics, articles for personal hygiene, deodorants or tensides, such as shampoos, soaps, disinfectants etc.

The compositions according to the invention may also contain further components, such as antioxidants, antimicrobials, odoriferous substances, dissolving intermediaries, etc.

The particular advantages of the compositions according to the invention compared to known compounds of this class are improved odoriferous quality, as well as improved spreading and penetration into human skin. Moreover, incorporation of the active compound into aqueous-alcoholic preparations in sufficient concentration is possible.

The dermatological agents prepared with undecenoic acid isopropylic ester can be applied without causing unpleasant odours and give excellent results in the case of mycoses of hairy and hairless skin, psoriasis, irritation of the scalp. excessive scurf, fatty seborrhea, acne and microspory and can be used in human as well as veterinary medicine.

The admixture with hydrotropic substances markedly widens the scope of the use.

The 10-undecenoic acid isopropylic ester can be prepared in several different ways:
1. undecenoic chloride can be admixed with isopropanol and heated in a water bath until the development of hydrogen chloride is terminated. The obtained ester is distilled off in vacuo.
2. It is also possible to obtain the ester by acid catalysis by means of ion exchangers.
3. An especially effective process is, however, the esterification catalyzed with mineral acids and azeotropic separation of water.

The following examples illustrate the invention.

EXAMPLE 1

Preparation of a lotion 1 percent by weight of 10-undecenoic acid isopropylic ester and 10 percent by weight of triacetine were dissolved under stirring in 50 percent by weight of isopropanol and then admixed with 50 percent by weight of distilled water.

EXAMPLE 2

Preparation of a skin oil 25 percent by weight of 10-undecenoic acid isopropylic ester were admixed under stirring with 75 percent by weight of adipic acid diisopropylic ester.

EXAMPLE 3

Preparation of a powder 10 percent by weight of 10-undecenoic acid isopropylic ester were sprayed in a spray mixer on to 10 percent by weight of fine silica particles and the obtained solid product was then admixed with 80 percent by weight of rice starch.

EXAMPLE 4

Remedy against fatty scalp and excessive dandruff formation 2 parts by weight of 10-undecenoic acid isopropylic ester
1 part by weight of triacetine
40 parts by weight of isopropylic alcohol
10 parts by weight of propanol are admixed and
47 parts by weight of distilled water are added to the mixture.

EXAMPLE 5

Gel as remedy for mycoses of the foot and against acne 10 parts by weight of undecenoic acid isopropylic ester
10 parts by weight of triacetine
20 parts by weight of adipic acid diisopropylic ester
55 parts by weight of palm-kernel oil first runnings [fatty acid ($C_6$ - $C_{18}$)-triglyceride ester]
5 to 10 parts by weight of montmorillonite are admixed under stirring and the mixture is then subjected in a Cowles-Dissolver having a peripheral velocity of 2 m sec. to intensive shearing force for a period of 15 minutes.

EXAMPLE 6

Foot spray

A mixture of 2 part by weight of undecenoic acid isopropylic ester
5 parts by weight of palm-kernel oil first runnings
1 part by weight of triacetine
87 parts by weight of isopropylic alcohol are filled into an aerosol container and
5 parts by weight of carbon dioxide are pressed into the container over the valve.

EXAMPLE 7

A man of 45 years with a severe, itchy mycosis in both auditory passages, which had been treated unsuccessfully for about 20 years with various well known remedies, was treated with pure, undiluted 10-undecenoic acid isopropylic ester. For this treatment a daily dosage of 1 drop of 10-undecenoic isopropylic ester was applied to each auditory passage. After two days treatment the itch disappeared and after one week the deseased skin of the auditory passages peeled off and new skin was formed. The new skin was no longer affected with mycosis and the patient had no longer any complaints.

EXAMPLE 8

A woman of 35 years suffered a case of severe fatty scalp so that the hair had to be washed every 12 hours. However, the use of known remedies against fatty scalp resulted in an excessive dandruff formation.

The remedy prepared according to example 4 was applied to the scalp of this woman. The remedy was successful to such an extent that after the first application, washing of the hair could be deferred for 3 days.

EXAMPLE 9

A 15 year old afflicted with excessive foot perspiration which caused an unpleasant odour (kakidrosis of the foot) and swelling.

After a foot bath the composition of example 6 was sprayed onto the patient's feet. After a regular daily use the unpleasant odour was no longer noticed. Within 2 weeks there were no longer any complaints.

What we claim is:

1. A method for the treatment of a fungal disease of the skin which comprises topical administration to the afflicted skin of a host of an amount of 10-undecenoic acid isopropylic ester which is therapeutically effective for the treatment thereof.

2. A method in accordance with claim 1 wherein the 10-undecenoic acid isopropylic ester is administered in a therapeutic composition containing from 0.1 to 50 percent by weight of ester, based on the total weight, in a pharmaceutically acceptable carrier.

3. A method in accordance with claim 1 wherein the 10-undecenoic acid isopropylic ester is administered in a therapeutic composition containing from 0.5 to 10 percent by weight of ester, based on the total weight, in a pharmaceutically acceptable carrier.

* * * * *